(12) United States Patent
Rajan Kesavelu Shekar et al.

(10) Patent No.: US 12,127,091 B2
(45) Date of Patent: Oct. 22, 2024

(54) WEARABLE SAFETY APPARATUS INCLUDING A BODY AREA NETWORK TRANSCEIVER

(71) Applicant: NXP B.V., Eindhoven (NL)

(72) Inventors: Pramod Rajan Kesavelu Shekar, Bangalore (IN); Rinze Ida Mechtildis Peter Meijer, Herkenbosch (NL); Anand Shirwal, Bangalore (IN)

(73) Assignee: NXP B.V., Eindhoven (NL)

( * ) Notice: Subject to any disclaimer, the term of this patent is extended or adjusted under 35 U.S.C. 154(b) by 224 days.

(21) Appl. No.: 17/449,967

(22) Filed: Oct. 5, 2021

(65) Prior Publication Data

US 2022/0141634 A1     May 5, 2022

(30) Foreign Application Priority Data

Nov. 5, 2020 (IN) .............................. 202011048375

(51) Int. Cl.
| | |
|---|---|
| *H04W 4/80* | (2018.01) |
| *G06F 1/16* | (2006.01) |
| *G16H 40/67* | (2018.01) |
| *H04B 1/3827* | (2015.01) |

(52) U.S. Cl.
CPC .............. *H04W 4/80* (2018.02); *G06F 1/163* (2013.01); *G16H 40/67* (2018.01); *H04B 1/385* (2013.01)

(58) Field of Classification Search
CPC .................................. H04W 4/80; H04B 1/385
See application file for complete search history.

(56) References Cited

U.S. PATENT DOCUMENTS

| | | | |
|---|---|---|---|
| 10,039,145 B2 | 7/2018 | Alipour et al. | |
| 2009/0002161 A1* | 1/2009 | Luciani ................ | A42B 3/0466 340/568.6 |
| 2014/0361871 A1* | 12/2014 | Silva ........................ | G07C 9/37 340/5.52 |

(Continued)

FOREIGN PATENT DOCUMENTS

WO     WO-89/02560     3/1989

OTHER PUBLICATIONS

Intrado GlobeNewswire; "Global Bike Helmet Market to Reach US813.89 Mn by 2025 as Number of Riders Rise"; QY Research; retrieved from the Internet https://www.globenewswire.com/news-release/2019/07/19/1885012/0/en/Global-Bike-Helmet-Market-to-Reach-US-813-89-Mn-by-2025-as-Number-of-Riders-Rise.html on Aug. 18, 2021; 4 pages (Jul. 18, 2019.

(Continued)

*Primary Examiner* — David Bilodeau

(57) ABSTRACT

A wearable safety apparatus including a body area network (BAN) transceiver for communicating with a user-controlled apparatus is described. The BAN transceiver includes a processor coupled to a BAN antenna. The processor is configured to receive an identification data request from a user-controlled apparatus in response to an action request of a user of the wearable safety apparatus; and to transmit identification data to the user-controlled apparatus in response to the identification data request. The identification data validates the user action by the user-controlled apparatus. The identification data request is only received when the wearable safety apparatus and the user-controlled apparatus are in contact with the user.

21 Claims, 9 Drawing Sheets

(56) References Cited

U.S. PATENT DOCUMENTS

| | | | | |
|---|---|---|---|---|
| 2016/0089075 | A1* | 3/2016 | Cowley | A61B 5/7475 |
| | | | | 600/300 |
| 2017/0136875 | A1* | 5/2017 | Logan | H04W 4/80 |
| 2017/0150333 | A1* | 5/2017 | Alsayyed Ahmad ... | B60R 25/24 |
| 2018/0338561 | A1* | 11/2018 | Destrian | G08B 25/10 |
| 2020/0145815 | A1 | 5/2020 | Taylor et al. | |
| 2022/0031947 | A1* | 2/2022 | Onesti | G16H 40/60 |

OTHER PUBLICATIONS

Langridge, Max; Pocket-Lint; "Apple files patents for 'earbuds with biometric sensing', health tracking capabilities on the horizon"; Retrieved from the Internet https://www.pocket-lint.com/headphones/news/apple/140581-apple-files-patents-for-earbuds-with-biometric-sensing-health-tracking-capabilities-on-the-horizon; 10 pages (Mar. 20, 2017).

Market Research Future; "Global Bike Helmet Market Size, Share, Trend, Growth and Global Overview—2027"; retrieved from the Internet https://www.marketresearchfuture.com/reports/bike-helmet-market-8022; 9 pages (Feb. 2021).

Markets and Markets; "HUD Helmet Market by Connectivity, Component Display, Outer Shell Material, Technology, End-User (Racing Professional, Personal Use), Function (Navigation, Communication, Performance Monitoring), Power Supply, and Region—Global Forecast to 2030"; retrieved from the Internet https://www.marketsandmarkets.com/Market-Reports/hud-helmet-market-258088609.html; 9 pages (Dec. 2019).

Siebert, Felix Wilhem et al; "Detecting motorcycle helmet use with deep learning"; Cornell University, Computer Science, Computer Vision and Pattern Recognition; retrieved from the Internet https://arxiv.org/abs/1910.13232; 28 pages (Oct. 29, 2019).

Sudarsan, K. et al; "Helmet for Road Hazard Warning with Wireless Bike Authentication and Traffic Adaptive Mp3 Playback," International Journal of Science and Research (IJSR) ISSN (Online): 2319-7064, vol. 3 Issue 3; 6 pages (Mar. 2014).

Vidhya, K. et al; "Smart Helmet & Bike System"; Intl. J. of Recent Technology and Enginering, vol. 7, Issue 4S2; 4 pages (Dec. 2018).

Wonghabut, P. et al.; "Automatic helmet-wearing detection for law enforcement using CCTV cameras"; IOP Conf. Ser.: Earth Environ. Sci. 143 012063; 8 pages (2018).

Muhammad Azizi, M. S. A. et al.; "Authentication with brainwaves: a review on the application of EEG as an authentication method"; 2018 Fourth International Conference on Advances in Computing, Communication & Automation; Oct. 2018; 6 pages.

Palaniappan, Ramaswamy et al.; "Biometrics from Brain Electrical Activity: A Machine Learning Approach"; IEEE Transactions On Pattern Analysis and Machine Intelligence; vol. 29, No. 4; Apr. 2007; 5 pages.

Pham, Tien et al.; "Multi-factor EEG-based User Authentication"; 2014 International Joint Conference on Neural Networks; Jul. 2014; 6 pages.

\* cited by examiner

WEARABLE SAFETY APPARATUS INCLUDING A BODY AREA NETWORK TRANSCEIVER

CROSS-REFERENCE TO RELATED APPLICATIONS

This application claims the priority under 35 U.S.C. § 119 of India patent application no. 202011048375, filed Nov. 5, 2020 the contents of which are incorporated by reference herein.

FIELD

This disclosure relates to a wearable safety apparatus with a body area network (BAN) transceiver. This disclosure further relates to a system with a wearable safety apparatus including a body area network transceiver and a user-controlled apparatus including a body area network transceiver.

BACKGROUND

Wearable safety apparatus such as helmets for example motorcycle or cycle helmets, eye protection, ear protection, safety gloves and other safety wear such as protective suits such as hazmat suits are used in a wide variety of applications. For example safety eyewear, ear protectors, and gloves may be required when operating equipment such as machine tools for example computer numerical control (CNC) lathes, industrial robots, and welding equipment. The use of machinery may be restricted to certain authorised users or operators who have appropriate training and only when wearing the appropriate protective equipment. Similarly, in many countries a motorcycle is typically only permitted to be ridden by a person wearing a motorcycle helmet.

SUMMARY

Various aspects of the disclosure are defined in the accompanying claims. In a first aspect there is provided a wearable safety apparatus comprising a body area network (BAN) transceiver, and a processor coupled to the BAN transceiver, wherein the processor is configured to receive an identification data request via the BAN transceiver from a user-controlled apparatus in response to an action request of a user of the wearable safety apparatus; and to transmit identification data via the BAN transceiver to the user-controlled apparatus in response to the identification data request, the identification data being for validation of the user action by the user-controlled apparatus; and wherein the identification data request is only received when the wearable safety apparatus and the user-controlled apparatus are in contact with the user.

In one or more embodiments, the processor may be further configured to retransmit the identification data to the user-controlled apparatus.

In one or more embodiments, the identification data may comprise at least one of wearable safety apparatus identifier data and user identifier data.

In one or more embodiments, the wearable safety apparatus may further comprise a biometric sensor and wherein the user identifier data comprises biometric data detected by the biometric data while the wearable safety apparatus is in contact with the user.

In one or more embodiments, the action request of a user may comprise an action for starting the user-controlled apparatus.

In one or more embodiments, the wearable safety apparatus may comprise one of a motorcycle helmet, a cycle helmet, eyewear, a body protection suit, and gloves.

In one or more embodiments, the wearable safety apparatus may further comprise a RF transceiver coupled to the processor, and wherein further data is transmitted and received via the RF transceiver. The RF transceiver may comprise one of an Ultra-Wide-Band (UWB) and Bluetooth Low Energy (LE) transceiver.

In one or more embodiments, the BAN transceiver may comprise a near-field electromagnetic induction (NFEMI) transceiver.

In a second aspect there is provided a user-controlled apparatus comprising a body area network, BAN, transceiver, and a processor coupled to the BAN transceiver, wherein the processor is configured to transmit an identification data request via the BAN transceiver in response to an action request of a user of a wearable safety apparatus; and to receive identification data via the BAN transceiver from the wearable safety apparatus in response to the identification data request, and wherein the processor is further configured to validate the user action request; and the identification data is only received when the apparatus and the wearable safety apparatus are in contact with the user.

In one or more embodiments, the processor may be further configured to check for retransmission of the identification data by the wearable safety apparatus and to invalidate the user action request if the identification data has not been received within a predetermined time.

In one or more embodiments, the identification data may further comprise at least one of least one of wearable safety apparatus identifier data and user identifier data and wherein the processor is further configured to validate the user action request by comparing the received identification data with a pre-determined wearable safety apparatus identifier data set and pre-determined user identifier data set.

In one or more embodiments, the user identifier data may comprise biometric data and wherein the apparatus is further configured to compare the biometric data with a predetermined biometric data set.

In one or more embodiments, the biometric data may comprise electroencephalogram (EEG) data and wherein during an enrolment phase the apparatus is configured to receive EEG data from the wearable device and to store the received EEG data and wherein the predetermined biometric data set comprises the received EEG data.

In one or more embodiments, the user-controlled apparatus may comprise a RF transceiver coupled to the processor, the RF transceiver configured to transmit and or receive further data to or from the wearable apparatus after the identification request has been validated.

In one or more embodiments, the RF transceiver may be configured as one of a UWB, and Bluetooth LE transceiver.

In one or more embodiments, the user-controlled apparatus may comprise one of an electric bicycle, a motorcycle, a machine tool, and a power tool.

In one or more embodiments, the BAN transceiver may comprise a near-field electromagnetic induction, NFEMI, transceiver.

Embodiments of the wearable safety apparatus and user-control apparatus may be included in a body area network communication system.

In a third aspect, there is provided body area network communication system comprising a wearable safety apparatus and a user-controlled apparatus, the wearable safety apparatus comprising a first body area network (BAN) transceiver and a first processor coupled to the first BAN transceiver, and the user controlled-apparatus comprising a second BAN transceiver and a second processor coupled to the second BAN transceiver; wherein the second processor is configured to: transmit an identification data request via the second BAN transceiver from the user-controlled apparatus to the wearable safety apparatus in response to an action request of a user;

the first processor is configured to transmit identification data via the first BAN transceiver from the wearable safety apparatus to the user-controlled apparatus in response to the identification data request; and the second processor is further configured to receive the identification data via the second BAN transceiver and to validate the user action request using the identification data; and wherein the identification data request is received by the wearable safety apparatus and the identification data is received by the user-controlled apparatus only when the wearable safety apparatus and the user-controlled apparatus are in contact with the user.

In a fourth aspect there is provided a method for operating a user-controlled apparatus comprising a first body-area-network, (BAN) transceiver, the user-controlled apparatus configured to be operated by a user wearing a wearable safety apparatus comprising a second BAN transceiver, wherein the user, the first BAN transceiver and the second BAN transceiver form a body-area-network, the method comprising:

transmitting an identification data request from the user-controlled apparatus to the wearable safety apparatus via the body-area-network in response to an action request of the user; transmitting identification data from the wearable safety apparatus to the user-controlled apparatus via the body-area-network in response to the identification data request; validating the user action request by the user-controlled apparatus using the identification data; wherein the identification data request is received by the wearable safety apparatus and the identification data is received by the user-controlled apparatus only when the wearable safety apparatus and the user-controlled apparatus are in contact with the user.

BRIEF DESCRIPTION OF THE DRAWINGS

In the figures and description like reference numerals refer to like features. Embodiments are now described in detail, by way of example only, illustrated by the accompanying drawings in which.

DETAILED DESCRIPTION

Figure 1:
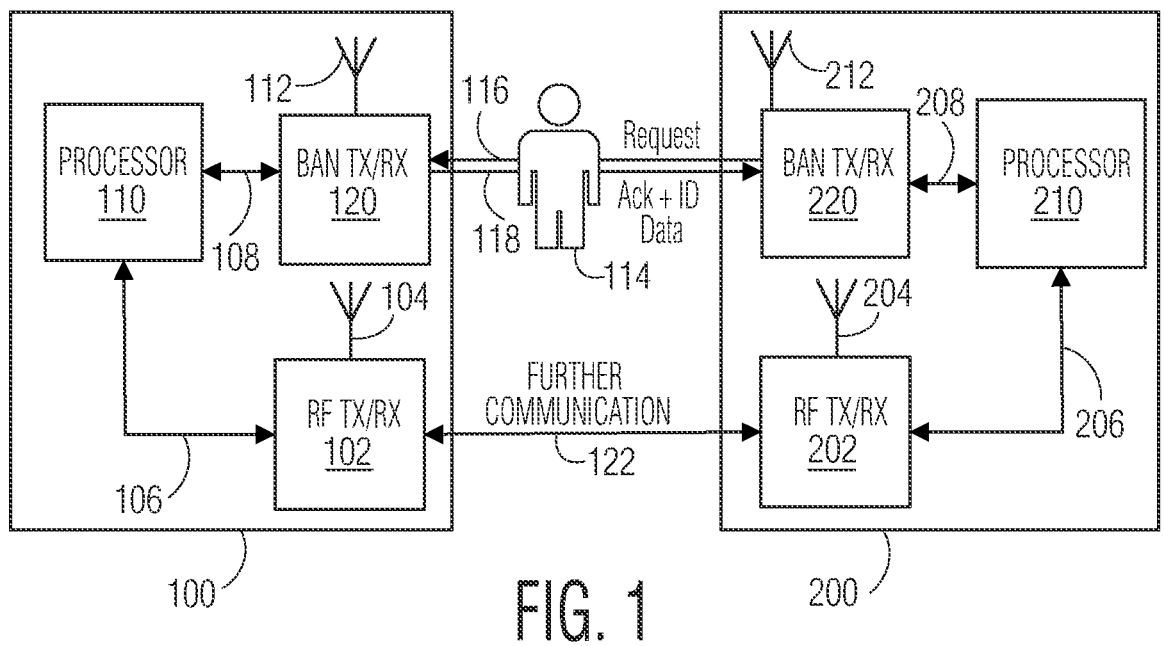
FIG. 1 shows a system including a wearable apparatus with a BAN transceiver and a user-controlled with a BAN transceiver according to an embodiment.

FIG. 1 shows a system including a wearable safety apparatus 100 with a BAN transceiver 120 and a user controlled apparatus 200 with a BAN transceiver 220 according to an embodiment. The user controlled apparatus 200 may also be referred to as an operator controlled apparatus. The wearable safety apparatus 100 may for example be protective eyewear such as spectacles or goggles, a protective helmet, ear defenders, a protective body suit or gloves. The wearable safety apparatus 100 has a processor 110 and optionally a radio-frequency (RF) transceiver 102. Examples of the RF transceiver may include but are not limited to a an Ultra-Wideband (UWB), a Bluetooth or WIFI transceiver. The term UWB transceiver as used herein includes transceivers implemented according to IEEE standard 802.15.4. The BAN transceiver 120 includes a BAN antenna 112. The RF transceiver 102 includes a RF transceiver antenna 104. The processor 110 may have a bidirectional connection 108 to the BAN transceiver 120 and a bidirectional connection 106 to the RF transceiver 102. The wearable safety apparatus 100 may be implemented in hardware or a combination of hardware and software.

The user controlled apparatus 200 may be as a non-limiting example a machine tool, industrial robot, welding equipment, or a motor vehicle such as a motorcycle or a car. The user controlled apparatus 200 has a processor 210 and optionally a RF transceiver 202. Examples of the RF transceiver may include but are not limited to an Ultra-Wideband (UWB), a Bluetooth or WIFI transceiver. The BAN transceiver 220 includes a BAN antenna 212. The RF transceiver 202 includes a RF transceiver antenna 204. The processor 210 may have a bidirectional connection 208 to the BAN transceiver 220 and a bidirectional connection 206 to the RF transceiver 202. The processor 210 may be implemented in hardware or a combination of hardware and software.

A BAN communication channel between the BAN transceivers 120 and 220 may be formed when a user 114 is coupled with both the BAN antenna 112 and the BAN antenna 212 by being simultaneously in contact with the wearable safety apparatus 100 and the user-controlled apparatus 200. Data may be transmitted from the user controlled apparatus 200 to the wearable safety apparatus 100 via communication channel or path 116 and data may be sent from the wearable safety apparatus 100 to the user controlled apparatus 200 via communication channel or path 118. The term user contact as referred to in the present disclosure may be a contact directly with the user 114 or may be an indirect contact via one or more items of clothing or other wearable that is being worn by the user 114. Examples of body area network (BAN) transceivers 120, 220 include a near field electromagnetic induction (NFEMI) transceiver, transceivers forming a body area network which uses the human body to form a communication path as described in IEEE Std 802.15.2-202, or other transceivers using human body-coupled communication.

Figure 2A:
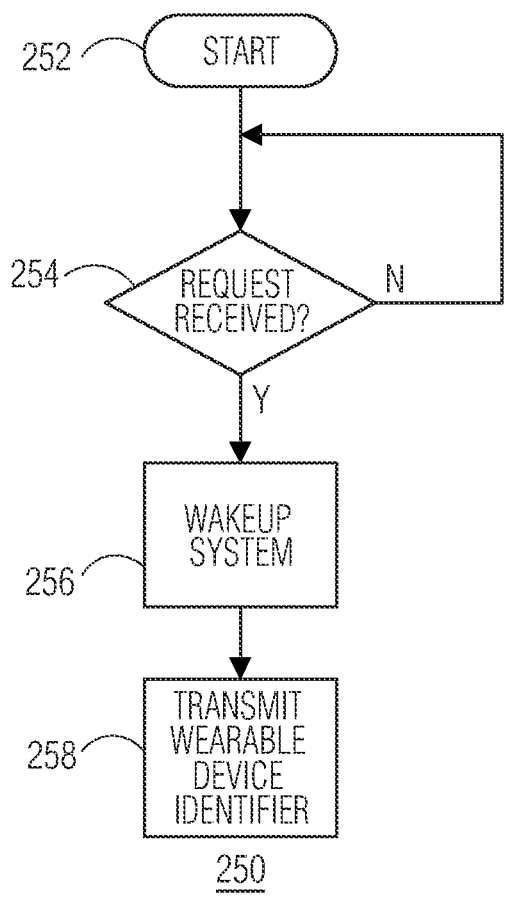
FIG. 2A shows a method of operation for the wearable safety apparatus illustrated in FIG. 1.
Figure 2B:
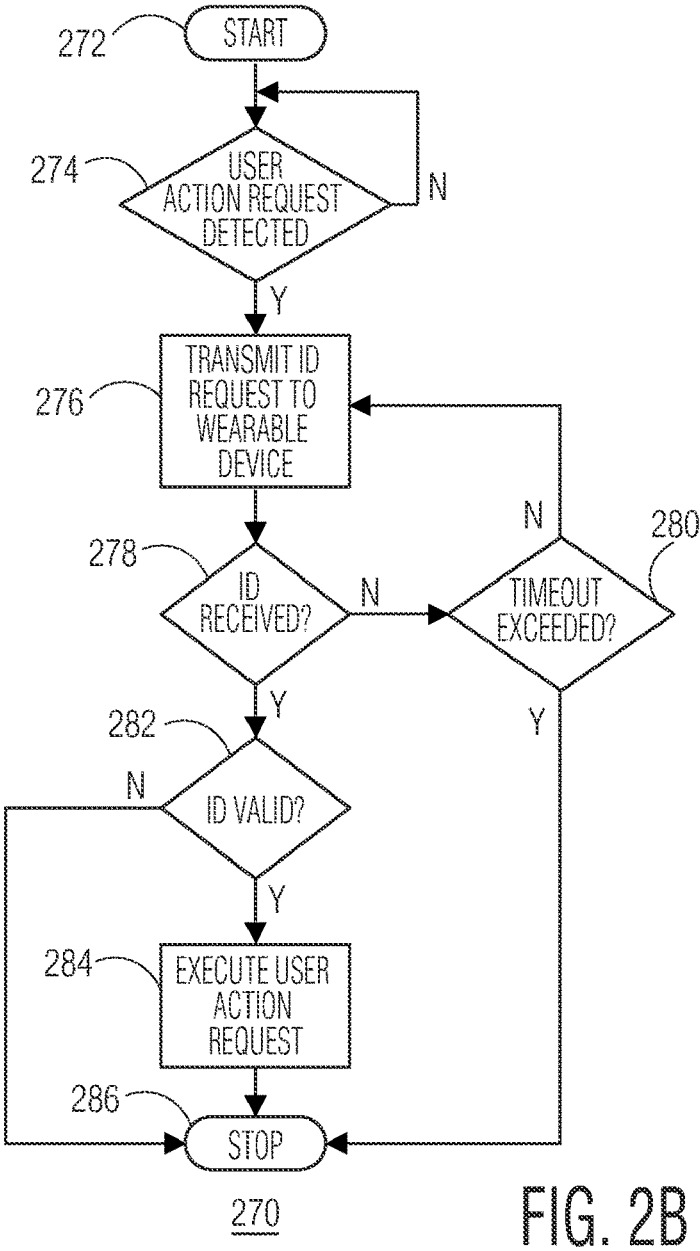
FIG. 2B shows a method of operation for the user-controlled apparatus illustrated in FIG. 1.

An example operation of the system illustrated in FIG. 1 is shown in FIGS. 2A and 2B.

FIG. 2A shows an example method of operation 250 which may be implemented by the wearable safety apparatus 100. In step 252 the method 250 starts. In step 254, the method may check if a request has been received via the BAN transceiver 120 from the user controlled apparatus 200. If a request has been received, then in optional step 256 elements of the system that were previously powered down may be powered up These elements may include for example the processor 110 and the RF transceiver 102. Once powered up, the processor 110 may receive the request directly or indirectly from the BAN transceiver. In step 258, the processor 110 may transmit an acknowledge together with identification data via the BAN transceiver 120 to the user controlled apparatus 200. This identification data may include the helmet identifier stored in the helmet identification module and/or a key stored in the tag key module 304.

FIG. 2B shows an example method of operation 270 for the user controlled apparatus 200. In step 272 the method 270 starts. In step 274, the method may check if a user action request has been received. This user action request may be for example be a request to start a motor in the user controlled apparatus 200. If a user request has been received, then in step 276 a request may be transmitted by the processor 210 via BAN transceiver 220. In step 278, the processor 210 may check to see whether identification data has been received via the BAN transceiver 220. If identification data has not been received then in step 280, the processor 210 may check to determine whether a timeout has been exceeded. If the timeout value has been exceeded then the method stops at step 286. If a timeout value has not been exceeded then the method returns to step 276 and the processor 210 may retransmit the ID request. Returning to step 278, if identification data has been received, then in step 282 the method checks if the ID data is valid. If the ID data is not valid, then the method ends at step 286. If the ID data is valid, then in step 284, the user action request is executed and the method ends at step 286.

Optionally, following the initial pairing operation of the wearable safety apparatus 100 and the user controlled apparatus 200, further communication 122 between the wearable safety apparatus 100 and the user controlled apparatus 200 may use the respective RF transceivers 102, 202. Subsequent communication may then be via the RF communication path following the initial authentication via the Body-Area-Network. In some examples this communication could be for example audio data communicated between the wearable apparatus and the user controlled apparatus. In some examples the RF transceivers 102,202 may not be used, and may be omitted.

The inventors of the present disclosure have appreciated that using a BAN communication channel between the wearable safety apparatus 100 and the user-controlled apparatus 200 can ensure that the user or operator is wearing the correct equipment before the user-controlled apparatus is actuated by checking the identification data. Since the user has to be in physical contact with both the wearable safety apparatus 100 and the motorcycle, the BAN communication channel provides a secure and simple way of ensuring that a user is authorised to operate the user-controlled apparatus 200.

Figure 3A:
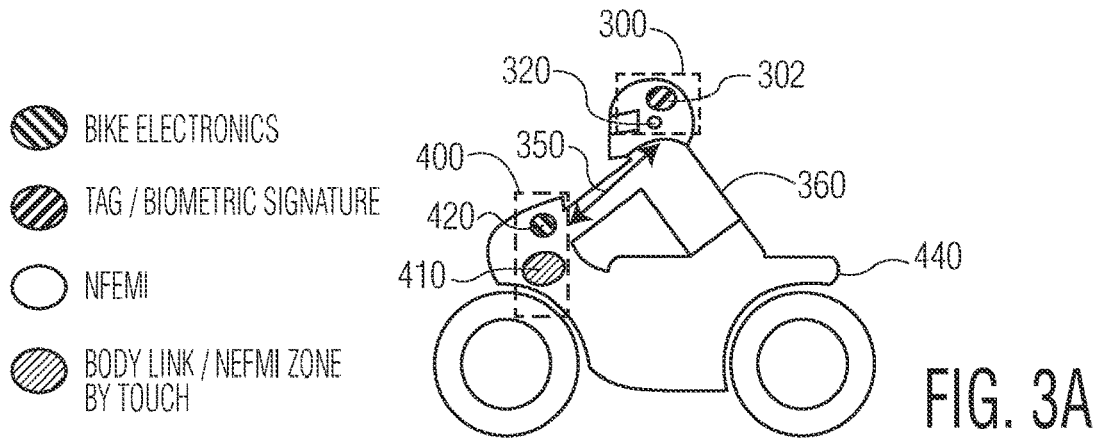
FIG. 3A shows a motorcycle helmet including an NFEMI transceiver according to an embodiment and a motorcycle including an NFEMI transceiver according to an embodiment.
Figure 3B:
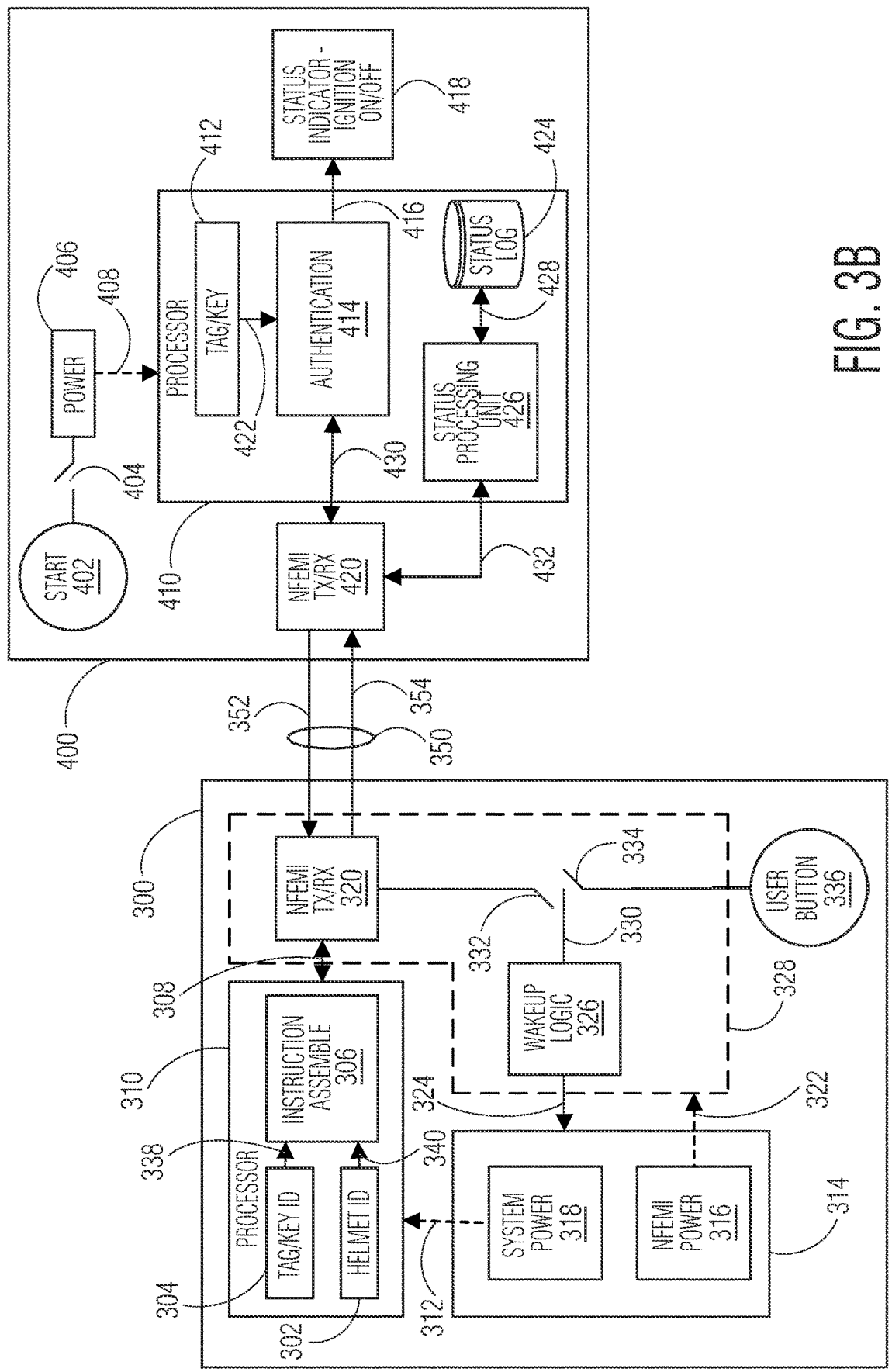
FIG. 3B shows a system including the NFEMI transceiver for a motorcycle helmet and a NFEMI transceiver for a motorcycle according to an embodiment.

FIG. 3A shows an apparatus including a motorcycle helmet NFEMI system 300 according to an embodiment and a motorcycle NFEMI system 400 according to an embodiment. FIG. 3B shows further details of the apparatus of FIG. 3A.

The motorcycle helmet NFEMI system 300 includes a processor 310, power control module 314, an NFEMI transceiver 320, wakeup logic 326, and user button 336.

The processor 310 may include a helmet identifier module 302 and tag or key identifier module 304 and instruction assembler 306. The tag identifier module 304 which may be a memory which stores the tag identifier may have an output 338 connected to an input of the instruction assembler 306. In some examples, the tag identifier module 304 may be omitted. The helmet identifier module 302 may include a memory which stores the helmet ID data. The helmet identifier module 302 may have an output 340 connected to the instruction assembler 306. The instruction assembler 306 may have a bidirectional connection 308 to the NFEMI transceiver 320. The user button 336 may be connected via switch 334 to wake-up logic input 330. The power module 314 may have a system power module 318 which supplies power to the processor 310 shown by the power connection 312. The system power module 318 may have an input connected to a wake-up logic output 324. The power module 314 may have an NFEMI power module 316 having a power connection 322 to an "always-on" power domain 328 which may include the NFEMI transceiver 320 and the wake-up logic 326. In some examples the NFEMI transceiver may be replaced with other BAN transceivers. In some examples an additional RF transceiver may be coupled to the processor 310 similar to the wearable safety apparatus 100.

The motorcycle control system 400 may include a start button 402 coupled via switch 404 to a power module 406. The power module 406 may provide power to a processor 410 via power connection 408. The motorcycle control system 400 may include an NFEMI transceiver 420 and a status indicator 418. The processor 410 may have a reference data module 412 having an output 422 connected to an authentication module 414. The reference data module may be a memory which includes authorized reference data such as valid helmet identification data and/or tag identification data and/or keys. The NFEMI transceiver 420 may have a bidirectional connection 430 to authentication module 414. The authentication module 414 may have an output 416 to a status indicator 418. The NFEMI transceiver 420 may have a bidirectional connection 432 to a status processing unit 426. The status processing unit 426 may have a bidirectional connection 428 to a status log module 424. In some examples the NFEMI transceiver may be replaced with other BAN transceivers. In some examples an additional RF transceiver may be coupled to the processor 410 similar to the user-controlled apparatus 200.

Figure 4A:
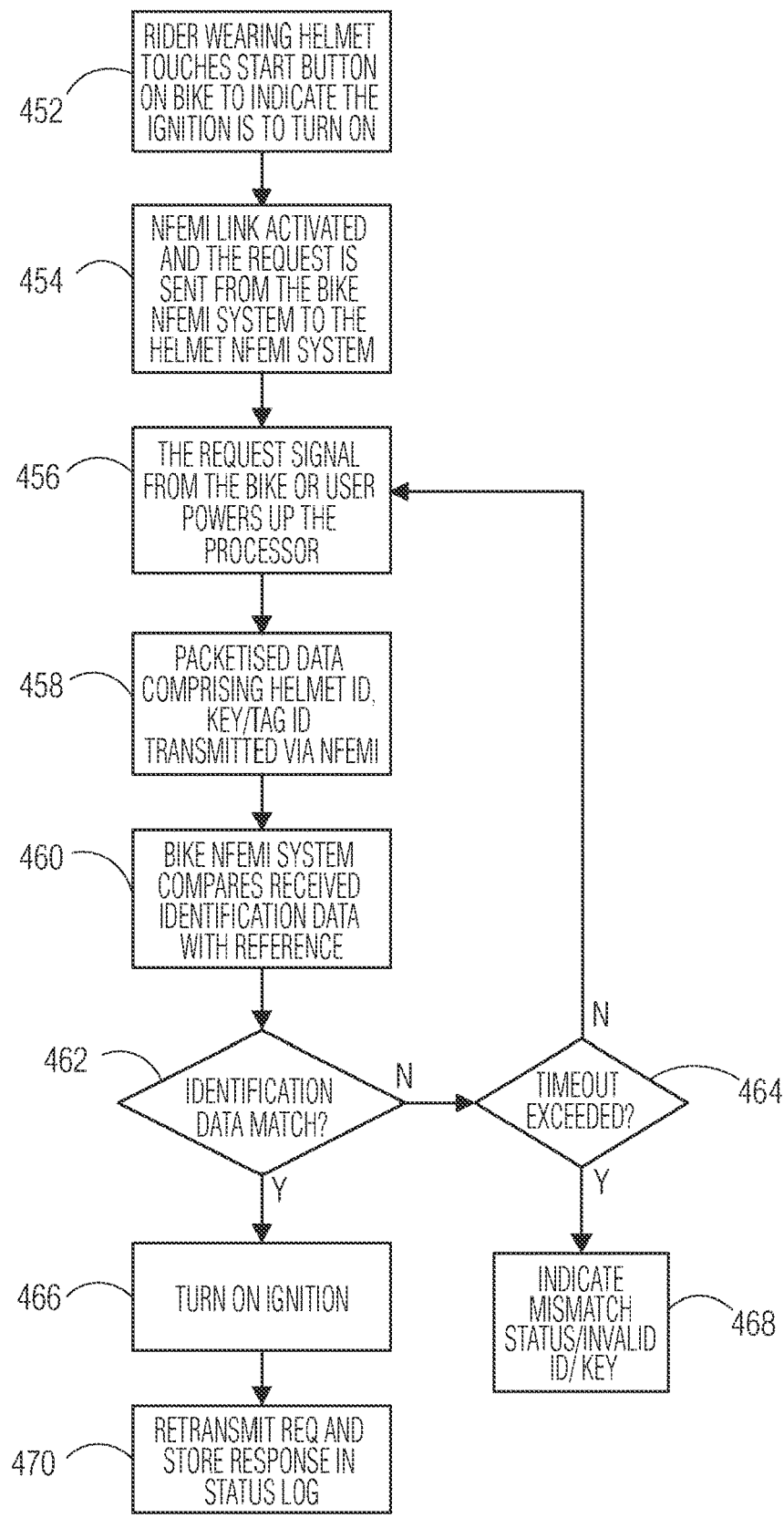
FIG. 4A shows a method of operation of the system of FIG. 3B.

FIG. 4A shows a method of operation 450 of the NFEMI communication system including the motorcycle helmet NFEMI system and motorcycle NFEMI system of FIGS. 3A and 3B. In step 452 a rider 360 wearing the helmet 300 may touch the start button 402 on the motorcycle 440 to indicate to the ignition to turn on. In step 454 the NFEMI link 350 may be activated by processor 410 and a request sent via channel 352 from the bike NFEMI system 400 to the helmet NFEMI system 300. This request may be transmitted by processor 410 via NFEMI transceiver 420. The NFEMI link 350 is only activated as a result of the rider 360 being in contact with both the helmet 300 and the motorbike 440. The body of the rider 360 therefore forms part of the communication channel 350 between the helmet NFEMI system 300 and the motorcycle NFEMI system 400. In step 456 the request signal received from the bike NFEMI system 400 may trigger the wake-up logic 326 to power up the processor 310 using the system power module 318. Alternatively in step 456 the user may power up the processor 310 by pressing user button 336 which also may trigger the wake-up logic 326 to power up the processor 310 using the system power module 318. The switches 332 and 334 which connect the user button 336 and the NFEMI transceiver 320 to the wake-up logic may be alternatively implemented using logic gates to implement for example a logic or function. Once powered up, the processor 310 may receive the request directly from the NFEMI transceiver 320. In other examples, the processor 310 may respond to the power up signal from the system power module 318 as a request to transmit identification data. In step 458 packet data comprising at least the helmet identification from the helmet ID module 302 and optionally a tag or key identifier from tag key identification module 304 may be assembled by the instruction assembler 306 and then the processor 310 may transmit the assembled instruction via the NFEMI transceiver 320 and via the channel 354 from the helmet NFEMI system 300 to the bike NFEMI system 400.

In step 460 the bike NFEMI system processor 410 may compare the identification data received via the NFEMI transceiver 420 with the reference data stored in the reference module 412 using the authentication module 414. In step 462 the authentication module 414 checks whether there is an identification data match. If there is an identification data match the method proceeds to step 466 and the ignition of the motorcycle 440 is turned on. Following on from step 466, optionally in step 470 the request may be retransmitted by the status processing unit 426. This retransmission may be a single or multiple retransmission. The response received from the helmet NFEMI system 300 may be logged in the status log module 424. Returning to step 462 if the identification data does not match, then the processor 410 may check in step 464 whether a timeout value has been exceeded. If the timeout value has not been exceeded then the method returns to 456 and the request signal is retransmitted. If the timeout value has been exceeded then in step 468 a mismatch may be indicated by the status indicator 418.

Figure 4B:
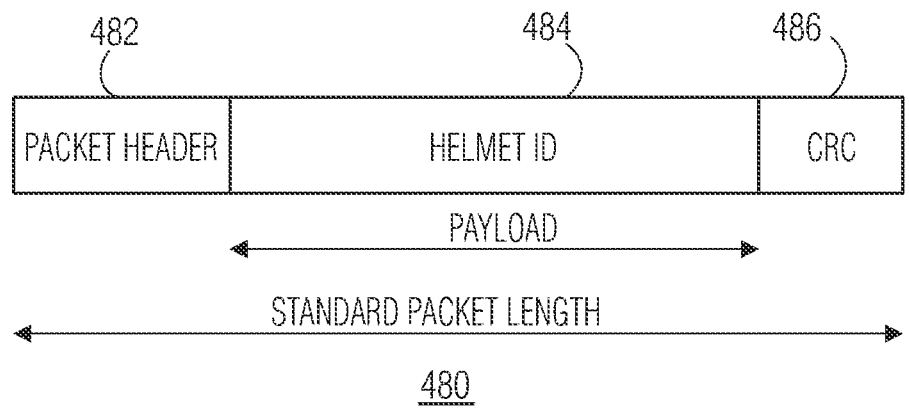
FIG. 4B shows an example packet for transmission by the NFEMI transceiver system for the helmet of FIG. 3B.
Figure 4C:
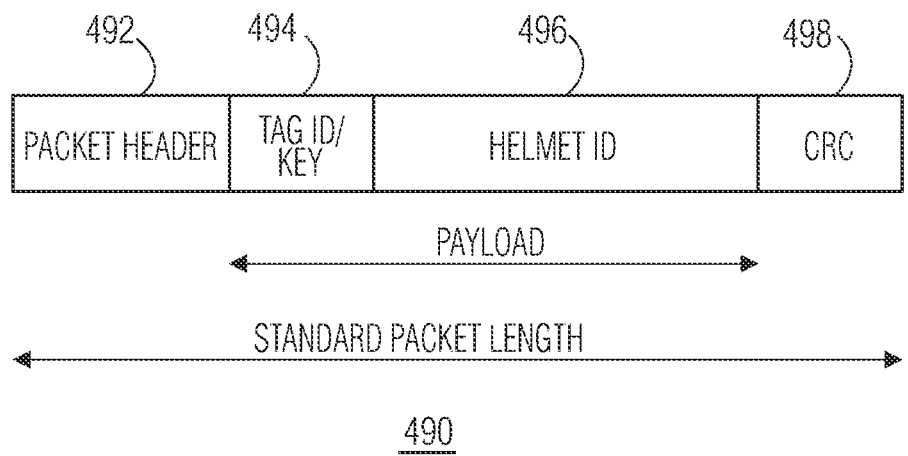
FIG. 4C shows an example packet for transmission by an NFEMI transceiver system for the helmet of FIG. 3B.

FIG. 4B shows an example packet 480 used to transmit a helmet identifier which consists of a packet header 482 payload which includes the helmet identifier 484 and a CRC check 486. FIG. 4C shows an example packet 490 used to transmit both a helmet identifier and a tag or key. Packet for 90 includes a packet header 492 payload consisting of a field for the tag identifier or key 494 and the helmet identifier 496 and finally a CRC check 498. Packets 480 and 490 may be assembled by the instruction assembler 306.

The inventors of the present disclosure have appreciated that using an NFEMI communication channel between the helmet of a rider and a motorcycle can ensure that the rider is wearing a helmet before the motorcycle is started by checking the helmet identification. Since the rider has to be in physical contact with both the helmet and the motorcycle, the NFEMI communication channel provides a secure and simple way of ensuring that a rider is authorised to ride the motorbike. Alternatively or in addition by having an additional tag identification or key, an additional authentication step may be made to determine that a particular rider is authorised to use the motorcycle. In addition by storing a status log by periodically transmitting requests from the motorcycle NFEMI system and receiving data back from the helmet, data may be stored showing whether the rider continues to wear the helmet for the entire duration of a trip. This information may be used for example by insurance providers to ensure whether the rider was wearing the helmet during a time of an accident. In some examples the motorbike with a physical key or fingerprint of the owner may act as a master key to configure or set the details of the unique helmet identifier in the motorbike during an initial enrolment phase of the helmet keys in the motorbike. The user may programme the list of keys in the bike with a master key. The keys may be multiple and shareable keys. Helmets including the NFEMI system may act as a shareable key with control limitations set by the user to control for example properties such as the maximum speed limit or distance that a user is allowed to ride.

Figure 5:
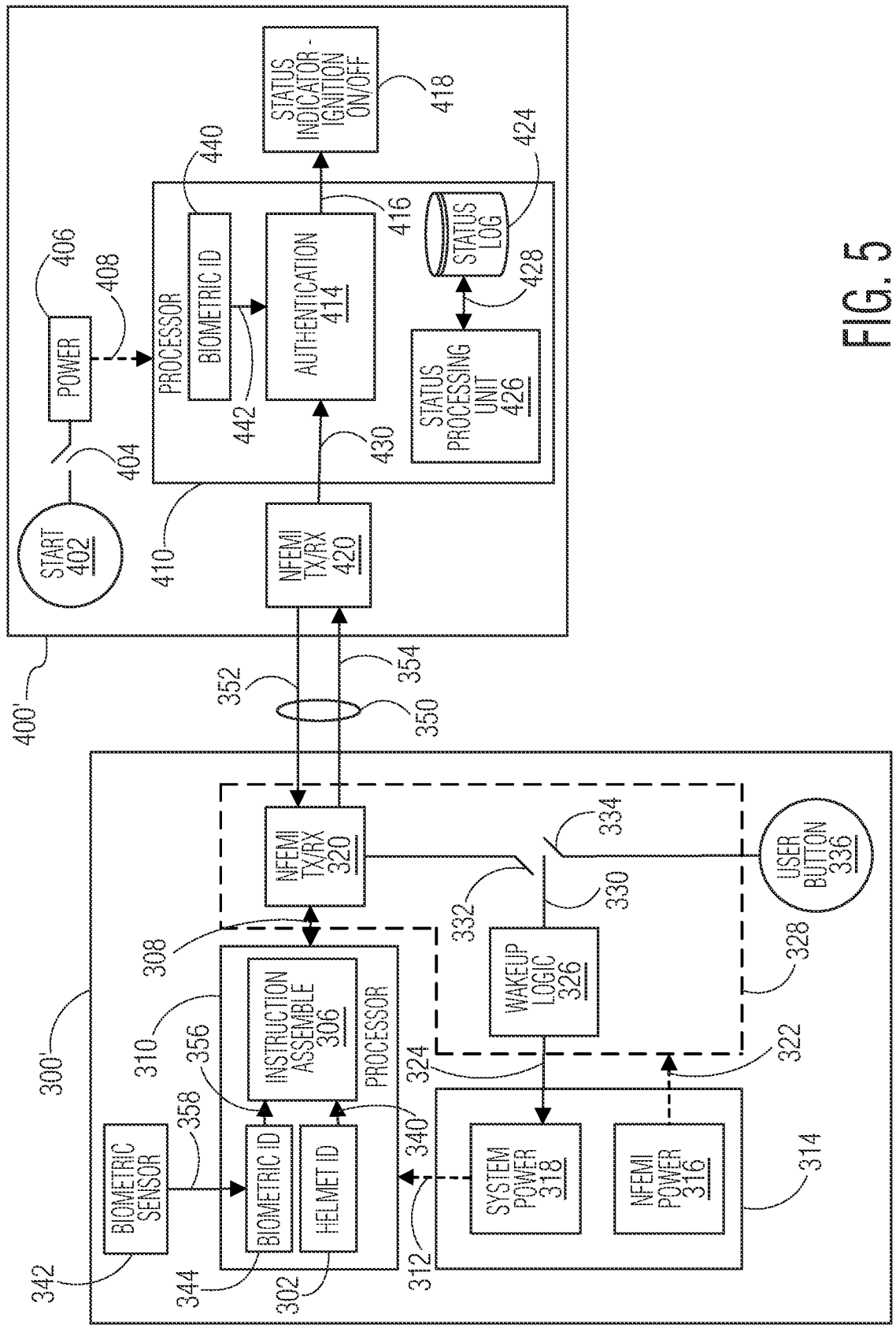
FIG. 5 shows an NFEMI transceiver system for a motorcycle helmet and a NFEMI transceiver system for a motorcycle according to an embodiment.

FIG. 5 shows an NFEMI transceiver system 300' for a motorcycle helmet and a NFEMI transceiver system 400' for a motorcycle according to an embodiment. The NFEMI transceiver system 300' has similar features to the NFEMI transceiver system 300 with the addition of a biometric sensor 342. The tag key ID module 304 is replaced with a biometric ID module 344 having an input connected to the biometric sensor output 358 and an output 356 connected to the instruction assembler module 306. Similarly motorcycle NFEMI transceiver system 400' has biometric ID module 440 having an output 442 to authentication module 414 instead of the tag module 412. The other features of motorcycle NFEMI transceiver system 400' are the same as motorcycle NFEMI transceiver system 400.

Figure 6:
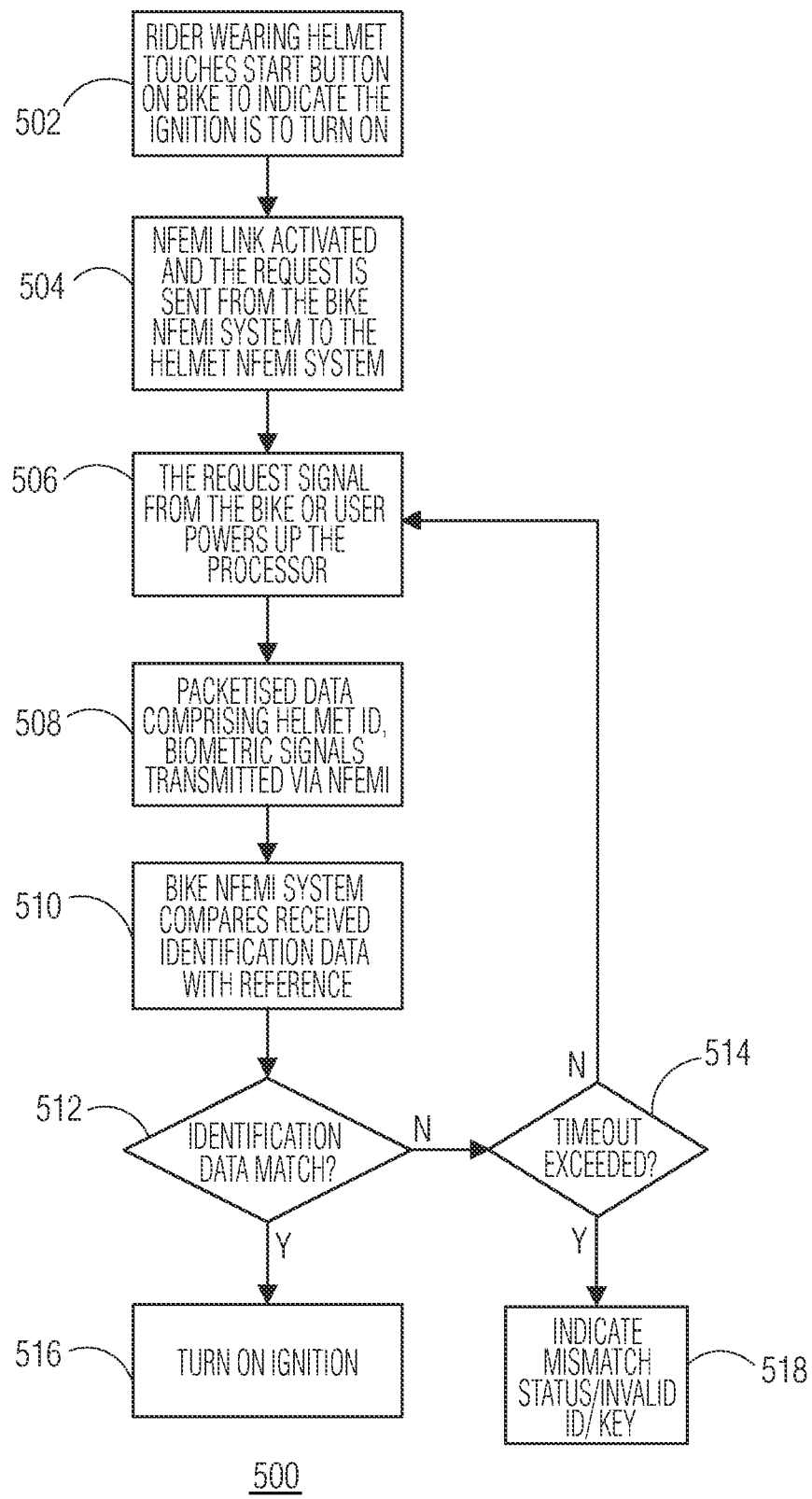
FIG. 6 shows a method of operation of the system of FIG. 5.

FIG. 6 shows a method of operation 500 of the motorcycle helmet and motorcycle control system of FIG. 5. In step 502 a rider wearing the helmet including the helmet NFEMI transceiver system 300' may touch the start button 402 on the motorcycle 442 to indicate to the ignition to turn on. In step 504 the NFEMI link 350 may be activated and a request 352 is sent from the bike NFEMI system 400' to the helmet NFEMI system 300'. The NFEMI link 350 is only activated as a result of the rider 360 being in contact with both the helmet 300 and the motorbike 440. The body of the rider 360 therefore forms part of the communication channel 350 between the helmet NFEMI system 300' and the motorcycle NFEMI system 400'. In step 506 the request signal received from the bike NFEMI system 400 may trigger the wake-up logic 326 to power up the processor 310 using the system power module 318. Alternatively in step 456 the user may power up the processor 310 by pressing user button 336 which also may trigger the wake-up logic 326 to power up the processor 310 using the system power module 318. The switches 332 and 334 which connect the user button 336 and the NFEMI transceiver 320 to the wake-up logic may be alternatively implemented using logic gates to implement for example a logic OR function. In step 508 packet data comprising biometric signals sensed by biometric sensor 342 which may be an EEG sensor are stored in biometric ID module 344. The stored biometric data and the helmet identification from the helmet ID module 302 may be assembled by the instruction assembler 306 and then transmitted by the processor 310 via the NFEMI transceiver 320 from the helmet NFEMI system 300' to the bike NFEMI system 400'.

In step 510 the bike NFEMI system 400' compares the received identification data with a reference using the authentication module 414. In step 512 the authentication module 412 checks whether there is an identification data match. If there is an identification data match the method proceeds to step 516 and the ignition of the motorcycle 440 is turned on. Returning to step 512 if the identification data does not match, then a check is made in step 514 as to whether a timeout has been exceeded. If the timeout has not been exceeded then the method returns to 506 and the request signal is retransmitted. If the timeout has been exceeded then in step 518 a mismatch is indicated on status indicator 418.

Figure 7:
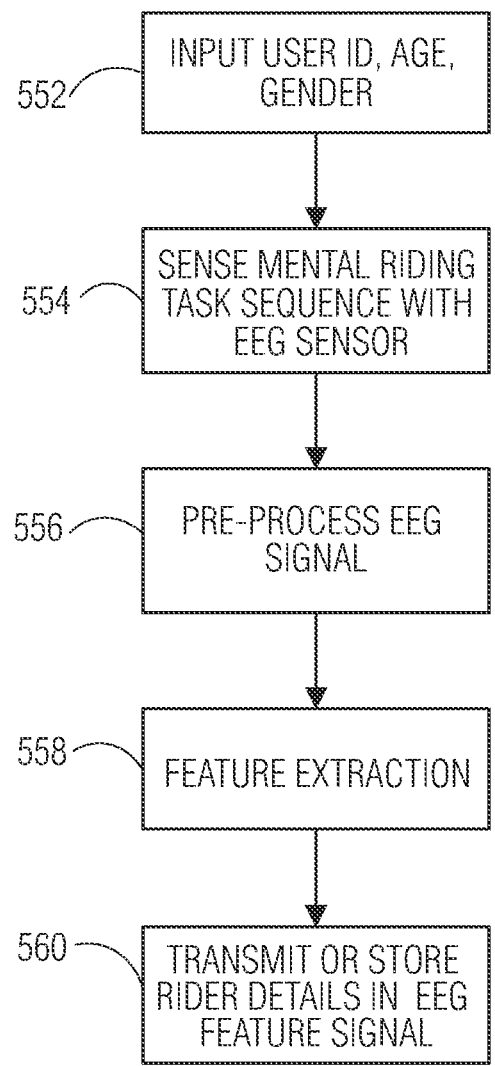
FIG. 7 shows a method of generating a biometric ID for transmission by the NFEMI transceiver system for a motorcycle helmet or for enrolment by the NFEMI transceiver system for a motorcycle.

FIG. 7 shows further detail of the method for biometric sensing using an EEG sensor 550. The method 550 may either be used by the motorcycle helmet NFEMI system 300' once the data request has been received or as part of an enrolment procedure to sense and store authorised biometric signatures in the motorcycle NFEMI system 400'. In step 552 a user ID age and gender may be received as an input. In step 554 an EEG sensor is enabled to sense a mental riding task sequence from a user or potential user of the motorcycle. In step 556 the EEG signal may be pre-processed. In step 558 features from the EEG may be extracted and in step 560 when used in enrolment the rider details may be stored in an EEG featured signal in the biometric ID module 440. Alternatively, when used for sensing by the helmet NFEMI transceiver system 300', the feature signal may be transmitted via the NFEMI transceiver 320.

Figure 8:
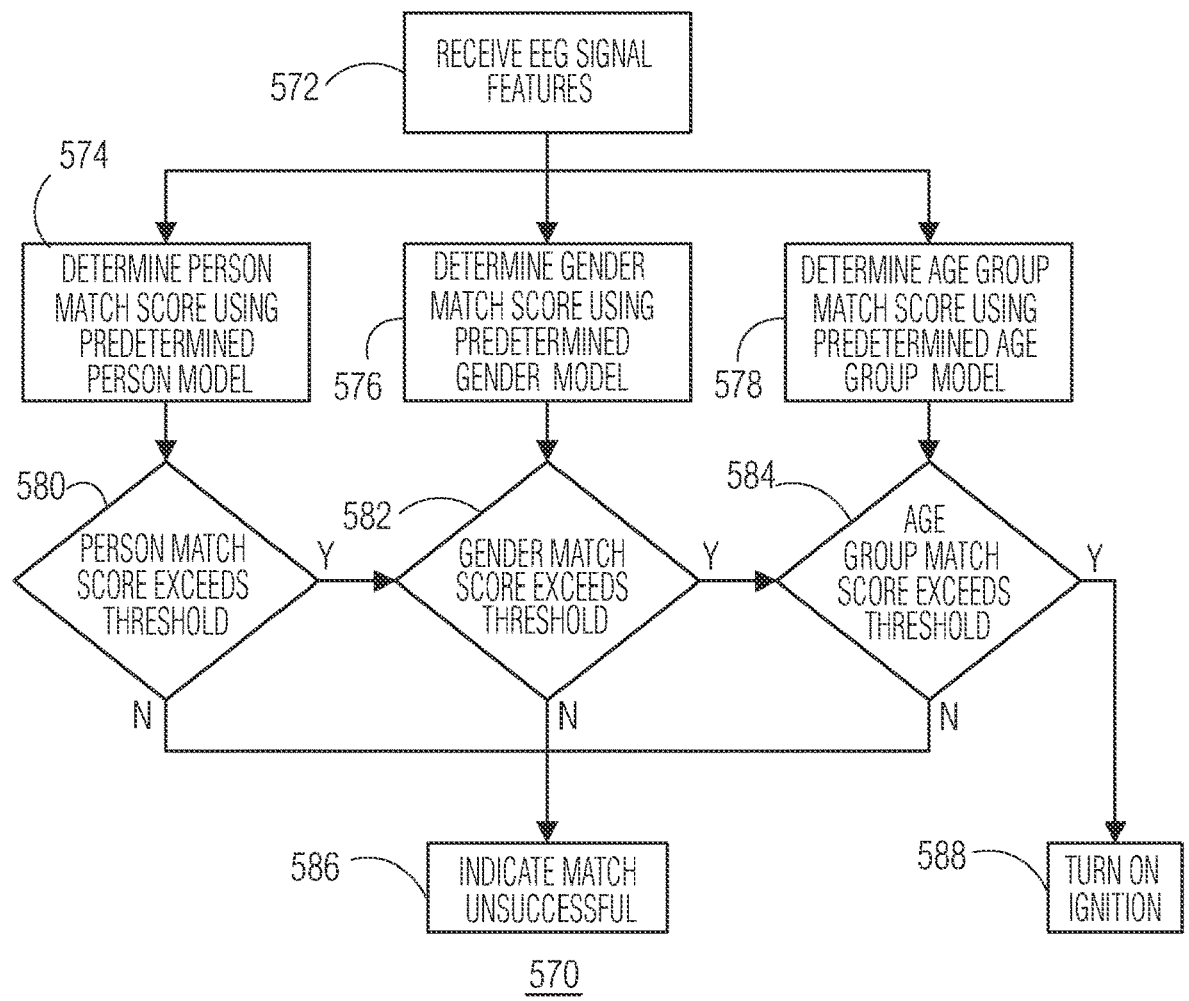
FIG. 8 shows a method of authenticating a biometric ID received by the NFEMI transceiver system for a motorcycle.

FIG. 8 shows a method of authentication using biometric EEG signals 570 that may be implemented for example by the authentication module 414. In step 572, the EEG signal features may be received. In step 574 a person match score may be determined using a predetermined person model. In step 580 a comparison is made to determine whether the person match score exceeds a threshold value. In parallel with step 574, in step 576 a gender match score may be determined using a predetermined agenda model. In step 582 a comparison is made to determine whether the gender match score exceeds a threshold value. Also in parallel with step 574, in step 578 an age group match score may be determined using a predetermined age-group model. In step 584 a comparison is made to determine whether the age group match score exceeds a threshold value. If any of the comparison steps 580,582, and 584 are unsuccessful, then in step 586 an indication is made that the biometric signature match is unsuccessful. If all the match scores in steps 580, 582 and 584 exceed the threshold values then in step 588 the ignition is turned on.

Figure 9:
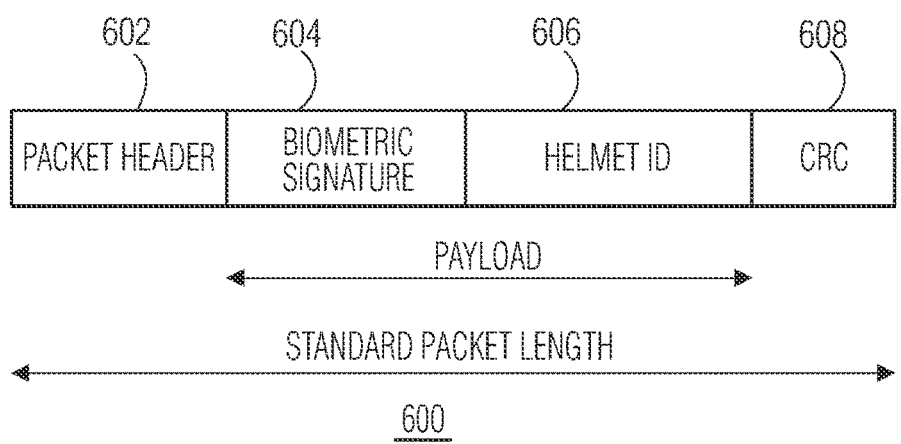
FIG. 9 shows an example packet for transmission by a NFEMI transceiver system operating according to the method of FIG. 7 and received by a NFEMI transceiver system operating according to the method of FIG. 8.

FIG. 9 shows an example data packet 600. Packet 600 includes a packet header 602 payload consisting of a biometric identifier 604 and the helmet identifier 606 and finally a CRC check 608. Packet 600 may be assembled by the instruction assembler 306.

Example methods of pre-processing and EEG classification are described for example in the following:

"Biometrics from Brain Electrical Activity: A Machine Learning Approach", Praniiappan and Mandic, IEEE Transactions on pattern analysis and machine intelligence vol 29, No 4, April 2007.

"Authentication with brainwaves: a review on the application of EEG as an authentication method", Azizi et al, IEEE 2018 Fourth International Conference on Advances in Computing, Communication & Automation (ICACCA), 26-28 Oct. 2018 Malaysia.

"Multi-factor EEG-based User Authentication", Pham et el, 2014 International Joint Conference on Neural Networks, July 2014, Beijing, China.

The system described in FIGS. 5,6,7 and 8 allows motorcycles to operate only when the rider is wearing a helmet. The purpose of this is two-fold: 1) to make use of electronics to help preventing bike usage with riders wearing a helmet for safety purposes, and 2) to obtain a biometric signature from the rider to be used to allow bike operation only for authorized user. The system makes use NFeMI radio technology to use the human body as channel, thereby allowing communication between helmet and motorcycle only when the rider is touching the bike, which may prevent any man-in-the-middle security attacks. The intelligent helmet is equipped with a unique ID tag and a EEG-based biometric sensing system for collecting a biometric signature of the rider when wearing the helmet. The motorcycle electronics initiate the NFeMI communication to detect the presence of the tag (i.e. the rider is wearing the helmet) and reads out the biometric signature of the helmet wearer. One or both elements are used to unlock the motorcycle for operation. Optionally this information can be logged for a trip.

Examples described herein include a helmet equipped with NFEMI radio technology, to communicate between helmet and bike via the human body (i.e. tag as a key to unlock the bike for operation by touch). NFEMI may be used for pairing with bike by touch. Further data centric communication can be enabled either via NFEMI, Bluetooth LE (BLE) or UWB or any other wireless communication technology. Helmet equipped with unique tag that is used to detect whether the rider is wearing the helmet. The tag may be read by the bike electronics by means of NFEMI. Helmets can act as a sharable key with a master command from user with set and/or predefined speed limits. In some examples a helmet or other wearable safety apparatus in contact with the head of a user may be equipped with EEG-based biometric sensing technology, and may collect a biometric signature of the rider for authorizing the usage of the bike. Bike electronics equipped with authentication process to authenticate the rider via tag (helmet use, i.e. safety) or biometric signature (EEG-based, i.e. security) etc. Interpretation of the signature and authentication process is done at the bike electronics to turn the ignition on or off. The helmet can be having wireless charging option, rechargeable battery. A bike owner can determine the maximum speed the shared person can ride. Bike electronics include an NFEMI system that log the status of rider wearing the helmet for the Insurance providers. Other examples may be used to pair a helmet or other wearable safety apparatus with another motor vehicle including a NFEMI transceiver.

In other examples, other wearable safety apparatus such as eyewear, ear-defenders and gloves including a NFEMI transceiver system and identification data may be used to communicate with other user-controlled equipment or vehicles including an NFEMI. Since the user forms at least the communication channel between the wearable safety apparatus and the user-controlled apparatus, this may allow secure authentication and/or verification that the correct safety apparatus is being worn prior to activating the user-controlled equipment.

A wearable safety apparatus including a body area network (BAN) transceiver for communicating with a user-controlled apparatus is described. The BAN transceiver includes a processor coupled to a BAN antenna. The processor is configured to receive an identification data request from a user-controlled apparatus in response to an action request of a user of the wearable safety apparatus; and to transmit identification data to the user-controlled in response to the identification data request. The identification data validates the user action by the user-controlled apparatus. The identification data request is only received when the wearable safety apparatus and the user-controlled apparatus are in contact with the user.

In some example embodiments the set of instructions/method steps described above are implemented as functional and software instructions embodied as a set of executable instructions which are effected on a computer or machine which is programmed with and controlled by said executable instructions. Such instructions are loaded for execution on a processor (such as one or more CPUs). The term processor includes microprocessors, microcontrollers, processor modules or subsystems (including one or more microprocessors or microcontrollers), or other control or computing devices. A processor can refer to a single component or to plural components.

In other examples, the set of instructions/methods illustrated herein and data and instructions associated therewith are stored in respective storage devices, which are implemented as one or more non-transient machine or computer-readable or computer-usable storage media or mediums. Such computer-readable or computer usable storage medium or media is (are) considered to be part of an article (or article of manufacture). An article or article of manufacture can refer to any manufactured single component or multiple components. The non-transient machine or computer usable media or mediums as defined herein excludes signals, but such media or mediums may be capable of receiving and processing information from signals and/or other transient mediums.

Example embodiments of the material discussed in this specification can be implemented in whole or in part through network, computer, or data based devices and/or services. These may include cloud, internet, intranet, mobile, desktop, processor, look-up table, microcontroller, consumer equipment, infrastructure, or other enabling devices and services. As may be used herein and in the claims, the following non-exclusive definitions are provided.

In one example, one or more instructions or steps discussed herein are automated. The terms automated or automatically (and like variations thereof) mean controlled operation of an apparatus, system, and/or process using computers and/or mechanical/electrical devices without the necessity of human intervention, observation, effort and/or decision.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub combination.

The applicant hereby gives notice that new claims may be formulated to such features and/or combinations of such features during the prosecution of the present application or of any further application derived therefrom.

For the sake of completeness it is also stated that the term "comprising" does not exclude other elements or steps, the term "a" or "an" does not exclude a plurality, a single processor or other unit may fulfil the functions of several means recited in the claims and reference signs in the claims shall not be construed as limiting the scope of the claims.

The invention claimed is:

1. A wearable safety apparatus comprising
a body area network, BAN, transceiver;
a processor coupled to the BAN transceiver,
wherein the processor is configured
to receive an identification data request via the BAN transceiver from a user-controlled apparatus in response to an action request of a user of the wearable safety apparatus; and
to transmit identification data via the BAN transceiver to the user-controlled apparatus in response to the identification data request,
the identification data being for validation of the action request by the user-controlled apparatus; and
wherein the identification data request is only received when the wearable safety apparatus and the user-controlled apparatus are in physical contact with the user.

2. The wearable safety apparatus of claim 1
wherein the processor is further configured to retransmit the identification data to the user-controlled apparatus.

3. The wearable safety apparatus of claim 1
wherein the identification data comprises at least one of wearable safety apparatus identifier data and user identifier data.

4. The wearable safety apparatus of claim 3 further comprising
a biometric sensor and wherein the identification data includes biometric data detected by the biometric sensor while the wearable safety apparatus is in physical contact with the user.

5. The wearable safety apparatus of claim 1
wherein the action request of a user comprises an action for starting the user-controlled apparatus.

6. The wearable safety apparatus of claim 1 comprising one of a helmet, a motorcycle helmet, a cycle helmet, eyewear, a body protection suit, and gloves.

7. The wearable safety apparatus of claim 1
wherein the BAN transceiver comprises a near-field electromagnetic induction, NFEMI, transceiver.

8. A user-controlled apparatus comprising
a body area network, BAN, transceiver, and
a processor coupled to the BAN transceiver,
wherein the processor is configured
to transmit an identification data request via the BAN transceiver in response to an action request of a user of a wearable safety apparatus; and
to receive identification data from the wearable safety apparatus in response to the identification data request, and
wherein the processor is further configured to validate the action request; and
wherein the identification data is only received when the apparatus and the wearable safety apparatus are in physical contact with the user.

9. The user-controlled apparatus of claim 8 wherein the processor is further configured
to check for retransmission of the identification data by the wearable safety apparatus and
to invalidate the user action request if the identification data has not been received within a predetermined time.

10. The user-controlled apparatus of claim 8
wherein the identification data comprises at least one of least one of wearable safety apparatus identifier data and user identifier data and
wherein the processor is further configured to validate the user action request by comparing the received identification data with a pre-determined wearable safety apparatus identifier data set and pre-determined user identifier data set.

11. The user-controlled apparatus of claim 8
wherein the user identifier data comprises biometric data and wherein the apparatus is further configured
to compare the biometric data with a predetermined biometric data set.

12. The user-controlled apparatus of claim 11
wherein the biometric data comprises EEG data and
wherein during an enrolment phase the apparatus is configured to receive EEG data from the wearable device and to store the received EEG data and
wherein the predetermined biometric data set comprises the received EEG data.

13. The user-controlled apparatus of claim 8
comprising one of a motor vehicle, a robot, an electric bicycle, a motorcycle, a machine tool, and a power tool.

14. The user-controlled apparatus of claim 8
wherein the BAN transceiver comprises a near-field electromagnetic induction (NFEMI) transceiver.

15. A body area network communication system comprising
a wearable safety apparatus and a user-controlled apparatus,
the wearable safety apparatus comprising
a first body area network (BAN) transceiver and
a first processor coupled to the first BAN transceiver, and the user controlled-apparatus comprising a second BAN transceiver and a second processor coupled to the second BAN transceiver;
wherein the second processor is configured to: transmit an identification data request via the second BAN transceiver from the user-controlled apparatus to the wearable safety apparatus in response to an action request of a user;
the first processor is configured to transmit identification data via the first BAN transceiver from the wearable safety apparatus to the user-controlled apparatus in response to the identification data request; and
the second processor is further configured to receive the identification data via the second BAN transceiver and to validate the action request using the identification data;
wherein the identification data request is received by the wearable safety apparatus and
wherein the identification data is received by the user-controlled apparatus only when the wearable safety apparatus and the user-controlled apparatus are in physical contact with the user.

16. A method for operating a user-controlled apparatus comprising
a first body-area-network, (BAN) transceiver, the user-controlled apparatus configured to be operated by a user wearing a wearable safety apparatus comprising a second BAN transceiver,
wherein the user, the first BAN transceiver and the second BAN transceiver are configurable to form a body-area-network, the method comprising:
transmitting an identification data request from the user-controlled apparatus to the wearable safety apparatus via the body-area-network in response to an action request of the user;
transmitting identification data from the wearable safety apparatus to the user-controlled apparatus via the body-area-network in response to the identification data request;
validating the action request by the user-controlled apparatus using the identification data;
wherein the identification data request is received by the wearable safety apparatus and
wherein the identification data is received by the user-controlled apparatus only when the wearable safety apparatus and the user-controlled apparatus are in physical contact with the user.

17. The wearable safety apparatus of claim 1:
wherein the identification data request is only received when both the wearable safety apparatus and the user-controlled apparatus are simultaneously in physical contact with the user.

18. The wearable safety apparatus of claim 1:
wherein the identification data request is only received when the user is wearing the wearable safety apparatus and the user is also touching the user-controlled apparatus.

19. The wearable safety apparatus of claim 1:
wherein the action request is a request to activate in the user-controlled equipment; and
wherein the user-controlled apparatus is not activated unless the user is wearing the wearable safety apparatus.

20. The wearable safety apparatus of claim 1:
wherein the action request is a request to start to operate the user-controlled equipment.

21. The wearable safety apparatus of claim 7:
wherein the wearable safety apparatus is a helmet;
wherein the user-controlled apparatus is a recreational vehicle;
wherein the user is a rider person; and
wherein an NFEMI link between the helmet and the recreational vehicle is only activated as a result of the rider person being in physical contact with both the helmet and the recreational vehicle.

* * * * *